United States Patent
Kypreos

[19]
[11] Patent Number: 5,879,771
[45] Date of Patent: Mar. 9, 1999

[54] FINGERTIP PROTECTOR FOR A PERSON USING A THERMAL APPLIANCE

[76] Inventor: Tony V. Kypreos, 1077 Martinstein Ave., Bay Shore, N.Y. 11706

[21] Appl. No.: 876,701

[22] Filed: Jun. 16, 1997

[51] Int. Cl.⁶ ................................................ A41D 13/00
[52] U.S. Cl. .............................. 428/64.1; 2/7; 2/16; 2/20; 2/163; 132/73.5; 428/42.1; 428/42.2; 428/42.3; 428/352; 428/354; 602/52; 602/58
[58] Field of Search ..................... 428/40.1, 64.1, 428/42.1, 42.2, 42.3, 352, 354; 132/73.5; 2/7, 16, 20, 163; 602/52, 58, 41

[56] References Cited

U.S. PATENT DOCUMENTS

| | | | |
|---|---|---|---|
| 3,348,541 | 10/1967 | Loebeck | 128/157 |
| 3,529,597 | 9/1970 | Fuzak | 128/157 |
| 4,751,747 | 6/1988 | Banks et al. | 2/21 |
| 4,803,755 | 2/1989 | Pohlman | 428/41.3 |
| 4,908,881 | 3/1990 | Field | 2/21 |
| 5,540,243 | 7/1996 | Simonton | 132/73 |
| 5,683,354 | 11/1997 | Levy | 602/54 |

*Primary Examiner*—Nasser Ahmad
*Attorney, Agent, or Firm*—Hoffmann & Baron, LLP

[57] ABSTRACT

A fingertip protector for a person using a thermal appliance includes a thermal insulation layer for thermally isolating the fingertip from the workpiece or work surface. The thermal insulation layer is sandwiched between an adhesive layer and preferably a heat-resistant, non-stick layer. The adhesive layer is used for securing the fingertip protector to a fingertip. The heat resistant, non-stick layer is used for preventing the work surface from adhering to the fingertip protector. The three layers are bonded to or laminated with one another to form a non-rigid pad which is adapted for mounting on the underside of a fingertip.

10 Claims, 3 Drawing Sheets

FINGERTIP PROTECTOR FOR A PERSON USING A THERMAL APPLIANCE

BACKGROUND OF THE INVENTION

1. Field of the Invention

The present invention relates to finger protection devices in general, and more particularly relates to a device used to provide thermal protection for the fingertip of a user of a thermal appliance.

2. Description of the Prior Art

In the craft-making field, it is often necessary to bond workpieces or work surfaces together using hot melt adhesives (hot glue). Using hot glue, as opposed to alternative bonding means, offers desirable features which include a fast setting time and a cleanup that is free from toxic solvents or the like. However, one disadvantage of using hot melt adhesives is that they are generally applied at temperatures between 300 and 450 degrees Fahrenheit. Because the work surfaces to be bonded together are typically held in place by a craft person's fingers until the glue has sufficiently set, severe burns to the person's fingertips are sometimes unavoidable without wearing some type of protective finger covering.

The use of gloves, in general, to protect hands and fingers from environmental hazards is well known in the prior art. Gloves have undergone numerous structural modifications, with each change tailored to a specific vocational or recreational application. The different materials from which these gloves have been fabricated are similarly numerous. The primary disadvantage of using glove-type coverings for protection, however, is that they are necessarily bulky in construction, and therefore unduly restrict hand and finger movement. Such restriction of movement can be detrimental in applications that require a high degree of manual dexterity. This is particularly true in the craft-making field, which typically involves the manipulation of small and delicate workpieces.

Although freedom of movement may generally be increased by employing a thinner glove material, or deleting the glove material from the finger portions altogether, the desirable thermal protection properties of the glove are accordingly diminished. Freedom of movement and thermal protection are generally mutually exclusive properties of a glove. Furthermore, gloves are cumbersome to put on and to take off, particularly when one or both hands are in use.

Other attempts at protecting the fingertip include the class of sheath-type devices, which are adapted to slide over the tip of the finger or thumb. For example, U.S. Pat. No. 4,908,881, to Field, discloses an aesthetically pleasing sheath-type finger guard to protect and cover an injured finger. However, the device disclosed in the Field Patent does not provide thermal protection to the wearer.

Another prior art device employing a sheath-type protective covering is disclosed in U.S. Pat. No. 4,751,747 to Banks. This device uses a thumb sheath and a pair of finger encompassing sheaths which are connected together by an insulating bridge therebetween. The device was specifically designed to provide thermal protection for use with hot curling irons, as found in the hair dressing field. Although sheath-type devices may offer improved freedom of movement of the hand, fingertip movement and tactile sensitivity remain substantially impaired.

Still other attempts at protecting the fingertip have concentrated on protecting the fingernail, rather than the underside portion of the fingertip. For example, U.S. Pat. No. 5,540,243, to Simonton, discloses a clip-on fingernail protector. This device, however, offers no protection, thermal or otherwise, for the underside portion of the fingertip.

Prior art protective finger coverings, attempting to provide thermal protection for the fingers, have been unsuccessful thus far for use in such applications as the craft-making field, which requires a high degree of manual dexterity. Therefore, there is a need, in such applications, to provide thermal protection for a thumb or finger that does not inhibit freedom of movement of the fingers or substantially impair tactile sensitivity.

OBJECTS AND SUMMARY OF THE INVENTION

It is an object of the present invention to provide a fingertip protection device for the user of a thermal appliance, such as a hot glue gun, which provides thermal protection for the tip of a human finger.

It is another object of the present invention to provide a fingertip protection device which provides thermal protection to the fingertip with negligible restriction of hand and finger movement and allows tactile, sensitivity to remain substantially unimpaired.

It is yet another object of the present invention to provide a fingertip protection device which has a substantially heat-resistant, non-stick surface, in order to minimize the adherence of a workpiece or work surface to the fingertip protector upon direct contact with a thermal adhesive applied to the workpiece or work surface.

It is a further object of the present invention to provide a fingertip protection device that is easy to use, can accommodate various finger sizes without modification and can be positioned on the fingertip precisely where protection is needed.

It is still a further object of the present invention to provide a fingertip protection device that is disposable and inexpensive to manufacture.

In accordance with one form of the present invention, there is provided a fingertip protector for a person using a thermal appliance, such as a hot glue gun, that includes a thermal insulation layer and is adapted to fit the underside of a human fingertip. The insulation layer is formed from a material having low thermal conductivity, such as cross-linked polyethylene foam, and provides thermal isolation between the fingertip and the contacted workpiece or work surface. The fingertip protector further includes an adhesive layer, which is preferably bonded to or laminated with the thermal insulation layer, for securing the fingertip protector to the fingertip.

The fingertip protector also preferably includes a heat-resistant, non-stick layer which is bonded to or laminated with the thermal insulation layer and opposite the adhesive layer. The non-stick layer provides a smooth surface having a low coefficient of friction which prevents the workpiece from adhering to the fingertip protector and also provides thermal protection for the insulation layer.

These and other objects, features and advantages of the present invention will become apparent from the following detailed description of illustrative embodiments thereof, which is to be read in connection with the accompanying drawings.

DETAILED DESCRIPTION OF THE PREFERRED EMBODIMENTS

Figure 1:
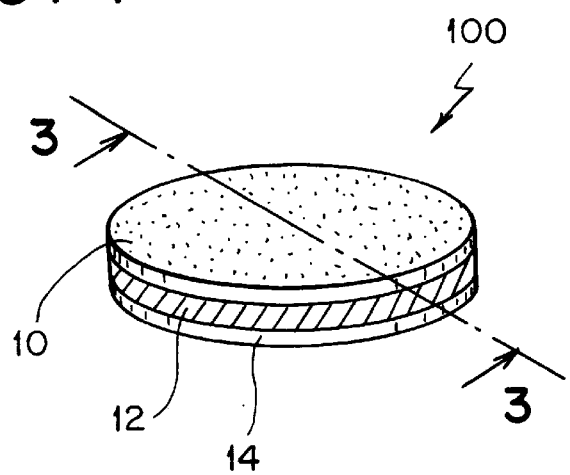
FIG. 1 is a perspective view of the fingertip protector formed in accordance with one form of the present invention.
Figure 2:
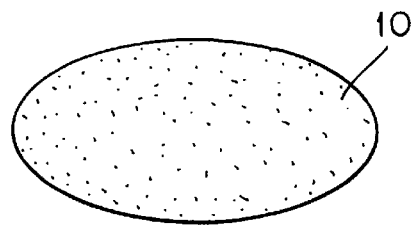
FIG. 2 is a top plan view of the fingertip protector shown in FIG. 1.
Figure 3:
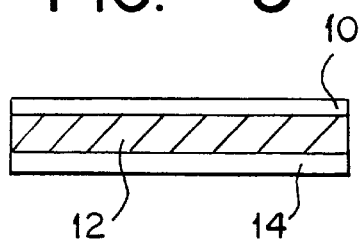
FIG. 3 is a cross-sectional view of the fingertip protector of FIGS. 1 and 2, taken along line 3—3 of FIG. 1.

Initially referring to FIGS. 1–3 of the drawings, a fingertip protector constructed in accordance with the present invention preferably includes three distinct components or layers. The layers are an adhesive layer 10, a thermal insulation layer 12 and preferably a non-stick layer 14. The layers are bonded to or laminated with one another to form a pad 100. The adhesive layer 10 and the non-stick layer 14 form opposite exterior surfaces of the pad 100. The pad 100 is sized and shaped, preferably as an ellipse, having a major axis and a minor axis which is normal to the major axis, to match the general shape and contours of a human fingertip.

The thermal insulation layer 12 comprises the core of the fingertip protector pad 100 and is situated between the adhesive layer 10 and the non-stick layer 14, assuming a non-stick layer is employed. The primary function of the thermal insulation layer 12 of the pad 100 is to provide thermal isolation between the fingertip and the exterior surface of the pad 100.

Consider, for example, an application involving the use of hot glue to bond two or more work surfaces together. Current hot melt glues are generally 100% polymeric materials which are reduced to molten thermoplastic materials by heating. A typical hot melt glue is a solid, thermoplastic hydrocarbon material which quickly melts when heated, and then sets to a bond on cooling. Hot melt adhesives are usually applied at temperatures of from about 300 to about 450 degrees Fahrenheit (°F.). Due to the high temperature of application, these products may cause severe burns if they come in contact with human skin. The thermal insulation layer 12 of the pad 100, therefore, prevents the heat from being transferred from the object being glued to the fingertip of a user, should the molten adhesive be contacted.

In addition to providing thermal isolation, the thermal insulation layer 12 serves as a support structure to which the adhesive layer 10 and non-stick layer 14 are bonded. Preferably, the thermal insulation layer 12 of the pad 100 is of unitary construction (i.e., one piece), although alternatively, it can be of laminate construction made of separate distinct components or layers which perform the same underlying function.

The thermal insulation layer 12 can be formed from any resilient material that can substantially reduce the transfer of heat through the fingertip protector pad 100. It is preferable that a material having low thermal conductivity be used, such as cross-linked polyethylene foam, which can reduce the transfer of heat through the pad 100 while maintaining sufficient flexibility. Numerous other materials having similar properties, including synthetic or natural latex rubbers, neoprene, cotton, silk, or polyurethane foams, may also be advantageously employed.

Figure 4:
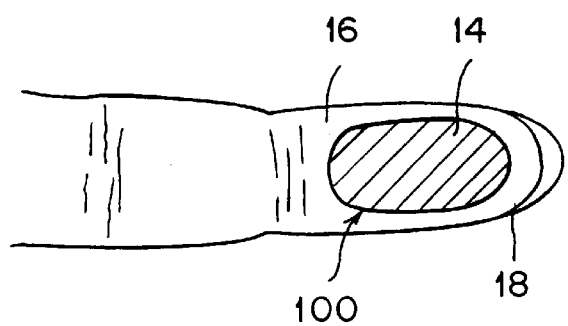
FIG. 4 is a bottom plan view of the underside of a fingertip illustrating the preferred mounting and placement of the fingertip protector, shown in FIGS. 1–3, on the fingertip.

Referring to FIG. 4, the fingertip protector pad 100 is preferably secured to the underside 16 of the fingertip 18 by means of the adhesive layer 10. The adhesive layer 10 is preferably formed as a coating that is applied to, or molded integrally with, a surface of the thermal insulation layer 12. Application of the adhesive layer 10 to the thermal insulation layer 12 in this manner lessens the chance of the bonded layers separating from one another. Moreover, forming the adhesive layer 10 as a coating, rather than as a distinct layer, provides a thinner resulting pad 100 and therefore provides less impairment of tactile sensitivity and less restriction of finger movement.

Although the adhesive layer 10 is preferably formed as a coating, the adhesive layer 10 may alternatively be formed from pressure-sensitive adhesive tape which is bonded to, or laminated with, the thermal insulation layer 12. The surfaces forming the junction between the insulation layer 12 and the adhesive layer 10 should provide an appropriate texture in order to achieve a suitable mechanical bond between the two layers.

Figure 4A:
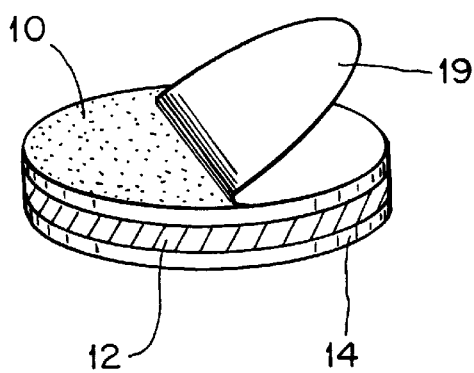
FIG. 4A is a perspective view of the fingertip protector shown in FIGS. 1–3 further illustrating a preferred peel-off protective strip, partially removed from the adhesive layer of the fingertip protector.

FIG. 4A illustrates a preferred embodiment of a fingertip protector pad 100 wherein the adhesive layer 10 of the pad 100 is covered by a peel-off strip 19 of protective material which prevents dust and the like from accumulating on the tacky adhesive surface. The peel-off protective strip 19 is removed at the time the pad 100 is mounted on the fingertip 18. The surface of the peel-off strip 19 that contacts the adhesive layer 10 of the pad 100 may be formed with a smooth, waxy coating or similar material, thereby enabling the fingertip pad 100 to be easily removed from the strip 19 without tearing or impairing the adhesive layer 10. Ideally, it is contemplated that the fingertip protector pads 100 be dispensed on a roll or on sheets. In this instance, the peel-off protective backing 19 would serve two functions: to keep dust and the like from adhering to the adhesive layer 10 and to hold the pads 100 to the sheet or roll for easy dispensing and storage.

Preferably, the surface of the fingertip protector pad 100 which will contact the work surface will include a heat-resistant, non-stick layer 14. This is desirable in applications involving the use of hot melt adhesives (hot glue), such as the craft-making art. One of the characteristics that make the use of hot melt adhesives so desirable, namely its fast setting time, also make it especially challenging to work with. Because the glue sets so quickly, it tends to undesirably bond to the craft person's fingers, which are often used to spread the glue or hold the workpieces together while the glue is setting.

The non-stick layer 14 of the fingertip protector pad 100 is selected to minimize bonding between the glue and the pad, should the pad inadvertently contact the hot glue. Furthermore, the non-stick layer 14 is preferably able to withstand temperatures in excess of about 450 degrees Fahrenheit, thereby providing thermal protection for the insulation layer 12 which may not be capable of withstanding direct contact with such temperatures. Cross-linked polyethylene foam, for instance, tends to melt at temperatures above about 250 degrees Fahrenheit.

It is preferred that the heat-resistant, non-stick layer 14 of the fingertip protector pad 100 be formed from a material having easy release characteristics and an inherently low coefficient of friction, such as Teflon™. However, other materials having similar properties may be used, such as Mylar™ or silicone coatings. Teflon™, in addition to its high temperature resistance and non-stick characteristics, is superior in that it may be easily laminated to or fusion bonded with the thermal insulation layer 12, thereby eliminating the need for adhesives.

While fusion bonding is preferred, adhesives may be used to bond the non-stick layer 14 to the thermal insulation layer 12. In this instance, the surfaces of the insulation layer 12 and non-stick layer 14 which are to be bonded together should provide an appropriate texture in order to achieve a suitable mechanical bond between the two layers. Additionally, it is contemplated that the thermal insulation layer 12 may be formed from a material that assimilates the desired characteristics of the non-stick layer 14. Specifically, in addition to providing thermal isolation, the material forming the thermal insulation layer 12 may also be heat-resistant and have easy release properties. In such case, the heat-resistant, non-stick layer 14 may be omitted.

Figure 5:
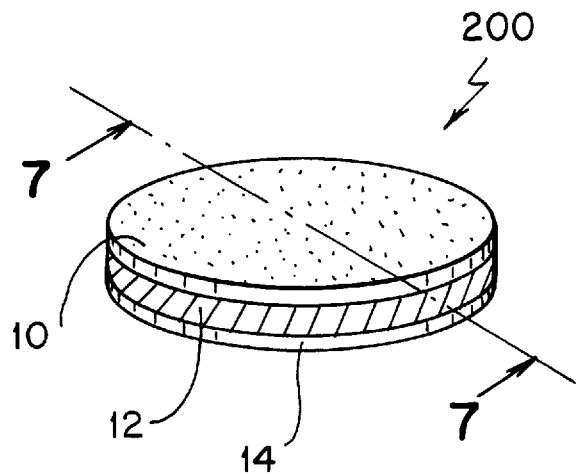
FIG. 5 is a perspective view of a second embodiment of the fingertip protector formed in accordance with the present invention.
Figure 6:
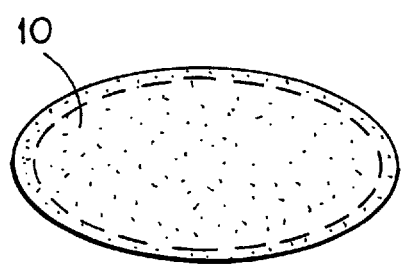
FIG. 6 is a top plan view of the fingertip protector shown in FIG. 5.
Figure 7:
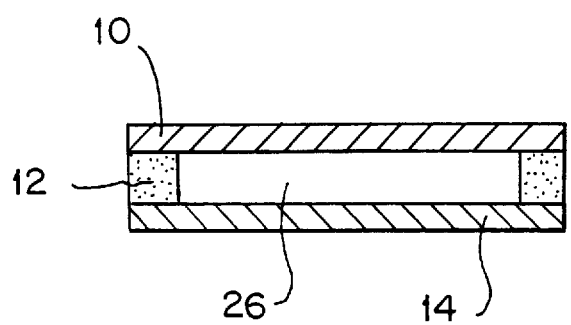
FIG. 7 is a cross-sectional view of the fingertip protector of FIGS. 5 and 6, taken along line 7—7 of FIG. 5.

Another embodiment of the present invention is illustrated in FIGS. 5–7 of the drawings. Referring to FIGS. 5–7, a fingertip protector pad 200 is primarily the same as the embodiment described above and shown in FIGS. 1–3, except for the construction of the thermal insulation layer 12. For the embodiment shown in FIGS. 5–7, the thermal insulation layer 12 of the fingertip protector pad 200 is formed as an annular ring which appropriately spaces the adhesive layer 10 from the non-stick layer 14 and which defines an interior air space 26. Forming the insulation layer 12 in this fashion takes advantage of the relatively low thermal conductivity of air by using the air space 26 itself as an insulator, rather than using a solid layer of insulating material, as in the embodiment of FIGS. 1–3.

Using an annular ring for the thermal insulation layer 12 of the pad 200 reduces the amount of insulation material necessary to form the pad 200 and furthermore reduces the rigidity of the pad 200. The width and rigidity of the annular ring used to form the insulation layer 12 should preferably be such that sufficient support is provided to prevent the adhesive layer 10 from contacting the non-stick layer 14.

Figure 8:
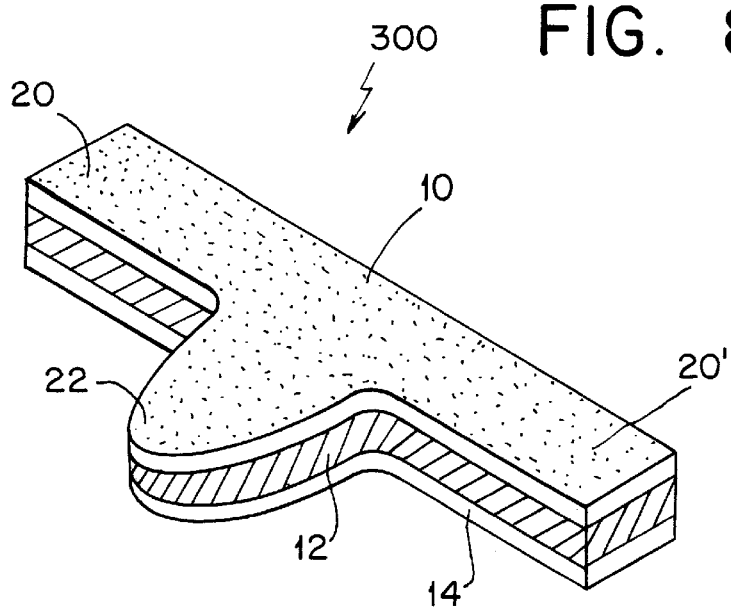
FIG. 8 is a perspective view of a third embodiment of the fingertip protector formed in accordance with the present invention.
Figure 9:
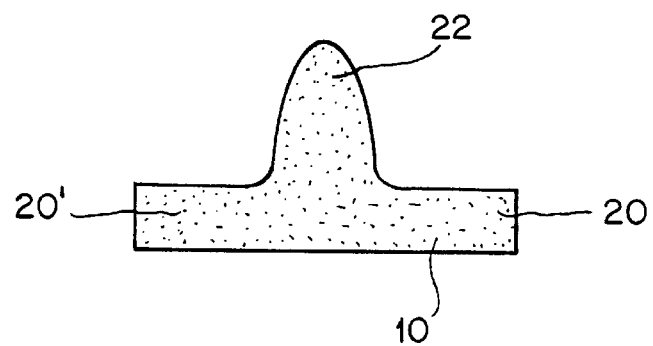
FIG. 9 is a top view of the fingertip protector shown in FIG. 8.
Figure 10:
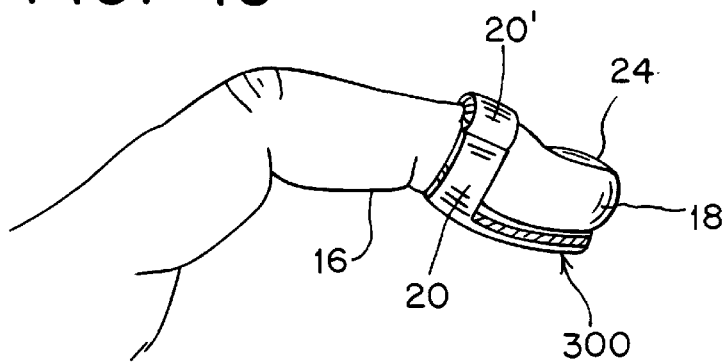
FIG. 10 is a perspective view illustrating the preferred mounting and placement of the fingertip protector of FIGS. 8 and 9 on the fingertip.

Yet another embodiment of the present invention is shown in FIGS. 8 and 9 of the drawings. In this embodiment, a fingertip protector pad 300 is formed having a substantially elliptical portion 22 with tab portions 20 and 20' extending out in laterally opposite directions along the minor axis (narrower dimension) of the elliptical portion 22. The tab sections 20 and 20' provide additional support for mounting the pad 300 on the underside 16 of the fingertip 18, as illustrated in FIG. 10. The tab portions 20 and 20' are preferably long enough to at least partially wrap around the fingertip 18 and are positioned most desirably so as not to contact the nail portion 24 of the fingertip 18 when the pad 300 is mounted thereon. Tab portions 20 and 20' may include all three layers 10, 12 and 14, as shown in FIG. 8, or alternatively may just include the adhesive layer 10. As mentioned previously, the tabs 20 and 20' may partially surround the user's fingertip, or may completely encircle the fingertip so that the tabs overlap and adhere to each other.

The dimensions of any of the fingertip protector pads 100, 200, and 300 discussed previously are not critical. The fingertip protector pads should be sized and shaped to provide ample coverage for the underside 16 of the fingertip 18 such that no bare skin is exposed which may directly contact the hot work surface. For the embodiment described above and shown in FIGS. 1–3, it is preferable that the major axis of the fingertip protector pad 100 have an axial length of about 1 inch and the minor axis have a lateral width of about ⅝ inch. While these dimensions were found to adequately fit most fingertips, the present invention contemplates different sized pads corresponding to the wide range of fingertip sizes.

Similarly, the overall thickness of any of the fingertip protector pads is not critical, as long as the pad provides sufficient thermal protection for the fingertip without a substantial loss of finger movement or tactile sensitivity. The required thickness will, of course, be directly affected by the material used in the manufacture of the insulation layer 12. For a fingertip protector pad 100 employing cross-linked polyethylene foam for the thermal insulation layer 12, an overall pad thickness of about ¹⁄₁₆ inch is preferred. A pad of this thickness provides good thermal isolation for the fingertip without substantially impairing tactile sensitivity or finger movement.

The use of an insulating material having comparatively lower thermal conductivity generally translates to a reduction in the required thickness of the thermal insulation layer 12 of the pad 100, resulting in a pad which is thinner overall. The thickness of the fingertip protector pad 100 will also be dependent on the application for which the pad is to be used. Applications involving direct contact with high surface temperatures (for example, above 450 degrees Fahrenheit) for a prolonged period of time (more than a few seconds) may necessarily require a thicker thermal insulation layer 12 for the pad 100.

A fingertip protector formed in accordance with the present invention provides thermal protection for the fingertip of a person using a thermal appliance, such as a hot glue gun typically employed in the craft-making art. Furthermore, the present invention provides such protection without substantially interfering with finger movement or tactile sensitivity. A fingertip protector formed in accordance with the present invention is easy to use and may be positioned on the fingertip to provide thermal protection at the precise area where such protection is needed. Moreover, because a fingertip protector of the present invention is simple in its construction, it is inexpensive to manufacture and would therefore justify disposal after each use.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A hot melt adhesive fingertip protector for providing thermal protection to a user of a thermal appliance, the fingertip protector comprising:

a pad securable to a fingertip of the user, the thermal protection pad including;

an adhesive layer for securing the pad to an underside surface of the fingertip; and a substantially heat-resistant, non-stick layer laminated to the adhesive layer, the non-stick layer is formed of polytetrafluoroethylene, polyester or silicone coating for applying said hot melt adhesive.

2. A fingertip protector as defined by claim 1, further comprising at least one thermal insulation layer situated between the adhesive layer and the heat-resistant, non-stick layer.

3. A fingertip protector as defined by claim 1, wherein the pad is sized and shaped so as to substantially fit a fingertip.

4. A fingertip protector as defined by claim 1, wherein the pad is substantially elliptical in shape and at least partially defined as having a major axis and a minor axis that is normal to the major axis.

5. A fingertip protector as defined by claim 1, further comprising:
   a first tab portion; and
   a second tab portion, the first and second tab portions affixed to the pad and extending laterally outward in opposite directions therefrom.

6. A fingertip protector as defined by claim 2, wherein the at least one thermal insulation layer is formed as a ring which, in combination with the adhesive layer and the heat-resistant non-stick layer, defines an interior air space.

7. A fingertip protector as defined by claim 1, wherein the adhesive layer is substantially continuous throughout the surface of the fingertip protector.

8. A fingertip protector as defined by claim 1, wherein the heat-resistant, non-stick layer is formed of a material able to withstand thermal communication with a substance having a temperature above about 300 degrees Fahrenheit.

9. A hot melt adhesive fingertip protector for protecting a fingertip of a user from burns while using a heated material, the fingertip protector comprising:
   an adhesive layer for securing the fingertip protector to an underside surface of the fingertip of the user;
   at least one thermal insulation layer situated adjacent to and laminated to the adhesive layer; and
   a substantially heat-resistant, non-stick layer situated adjacent to and laminated to the at least one thermal insulation layer and opposite the adhesive layer, the layers together forming a pad; said non-stick layer is formed of polytetrafluoroethylene, polyester or silicone coating; the non-stick layer is for applying said hot melt adhesive.

10. A method of protecting a fingertip of a user while spreading hot melt adhesive, the method comprising the steps of:
   (a) providing a hot melt adhesive fingertip protector pad sized to fit the fingertip of the user, the protector pad including an adhesive layer for securing the pad to an underside surface of the fingertip and a substantially heat-resistant, non-stick layer situated adjacent to and laminated to the adhesive layer; said non-stick layer is formed of polytetrafluoroethylene, polyester or silicone coating; and
   (b) securing the protector pad to the fingertip of the user so that the protector pad substantially covers the underside surface of the fingertip, wherein the fingertip of the user is protected from direct thermal contact with the hot melt adhesive.

* * * * *